United States Patent [19]
Bedeschi et al.

[11] Patent Number: 5,998,426
[45] Date of Patent: *Dec. 7, 1999

[54] 9,10 DISUBSTITUTED CAMPTOTHECIN DERIVATIVES WITH ANTITUMOR ACTIVITY

[75] Inventors: Angelo Bedeschi, Milan; Walter Cabri, Rozzano; Ilaria Candiani, Busto Arsizio; Franco Zarini, Settimo Milanese; Sergio Penco, Milan, all of Italy

[73] Assignee: Pharmacia & Upjohn S.p.A., Milan, Italy

[ * ] Notice: This patent is subject to a terminal disclaimer.

[21] Appl. No.: 08/913,855

[22] PCT Filed: Jan. 11, 1997

[86] PCT No.: PCT/EP97/00194

§ 371 Date: Sep. 29, 1997

§ 102(e) Date: Sep. 29, 1997

[87] PCT Pub. No.: WO97/28164

PCT Pub. Date: Aug. 7, 1997

[30] Foreign Application Priority Data

Jan. 30, 1996 [GB] United Kingdom ................ 9601779

[51] Int. Cl.$^6$ .................... C07D 491/22; A61K 31/47
[52] U.S. Cl. ............................... 514/283; 546/48
[58] Field of Search ................ 546/46, 48; 514/283

[56] References Cited

U.S. PATENT DOCUMENTS 5,614,628  3/1997  Cabri et al. .................... 546/48

FOREIGN PATENT DOCUMENTS 91-05556   5/1991   WIPO .
92-05785   4/1992   WIPO .
95-09169   4/1995   WIPO .
95-22549   8/1995   WIPO .
95-28404  10/1995   WIPO .

OTHER PUBLICATIONS

Hsiang et al, Cancer Res. vol 49 pp. 4385–4389 (1989).
Wani et al, J. Med, Chem, vol 29 pp. 2358–2363 (1986).
Kingsbury et al. J. Med. Chem vol 34 pp. 98–100 (1991).

*Primary Examiner*—Mukund J. Shah
*Assistant Examiner*—Bruck Kifle
*Attorney, Agent, or Firm*—Oblon, Spivak, McClelland, Maier & Neustadt, P.C.

[57] ABSTRACT

The present invention relates to 9-amino-10-(1-naphthylsulfonyloxy)-20(S)-camptothecin, 9-amino-10-phenylsulfonyloxy-20(S)-camptothecin, 7-ethyl-9-amino-10-(p-toluensulfonyloxy)-20(S)-camptothecin, their pharmaceutically acceptable salts, a process for their preparation, pharmaceutically compositions comprising them and their use as antitumor agents.

10 Claims, No Drawings

9,10 DISUBSTITUTED CAMPTOTHECIN DERIVATIVES WITH ANTITUMOR ACTIVITY

The present invention relates to 9,10 disubstituted camptothecin derivatives, to a process for their preparation, to a pharmaceutically composition comprising them and to their use as antitumor agents.

Our previous International Patent Application WO 95/09169 discloses a general class of disubstituted camptothecin derivatives.

It has now been found that certain 9,10 disubstituted camptothecin derivatives, not specifically disclosed in WO 95/09169, possess excellent antitumor activity.

Accordingly, the present invention provides a 9,10 disubstiluted camptolhecin derivative of formula (Ia)

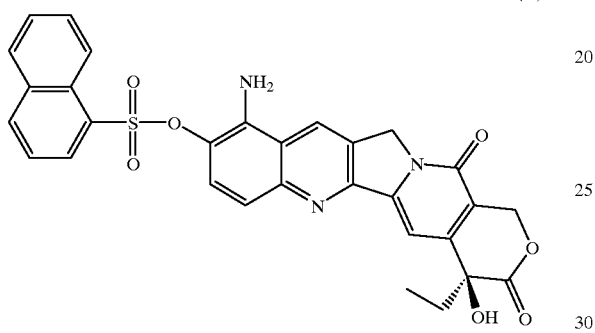

(Ia)

namely: 9-amino-10-(1-naphthylsulfonyloxy)-20(S)-camptothecin;
a 9,10 disubstituted camptothecin derivative of formula (Ib)

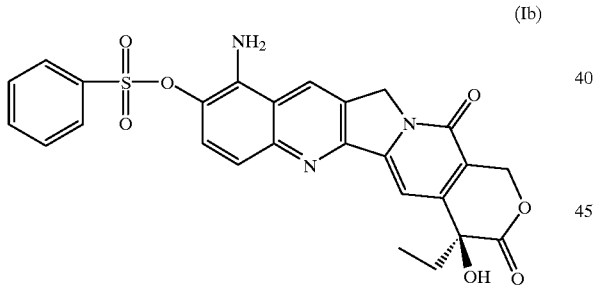

(Ib)

namely: 9-amino-10-phenylsulfonyloxy-20(S)-camptothecin; a 9,10 disubstituted camptothecin derivative of formula (Ic)

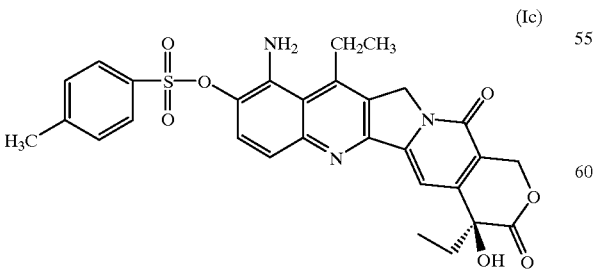

(Ic)

namely: 7-ethyl-9-amino-10-(p-toluensulfonyloxy)-20(S)-camplothecin;

and the pharmaceutically acceptable salts thereof.

The pharmaceutically acceptable salts of the above compounds include salts with pharmaceutically acceptable acids, either inorganic acids, such as e.g., hydrochloric, hydrobromic, nitric, or sulphuric acid or organic acids, such as e.g., citric, tartaric, maleic, fumaric, methanesulfonic or ethanesulfonic acid.

The above compounds may be prepared by a process which comprises:

(1) nitrating a compound of formula (II)

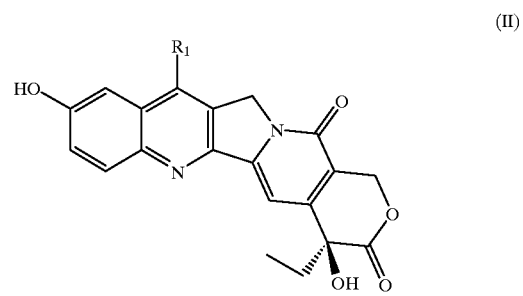

(II)

wherein $R_1$ is hydrogen or ethyl, to obtain a compound of formula (III):

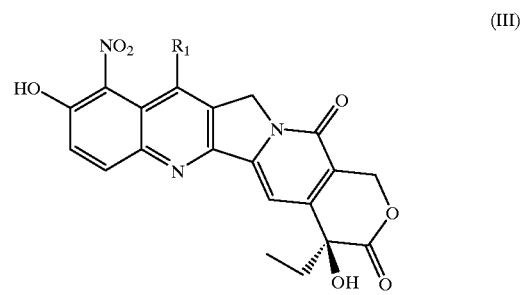

(III)

wherein $R_1$ is as defined above;

(2) converting the compound of formula (III) into a compound of formula (V):

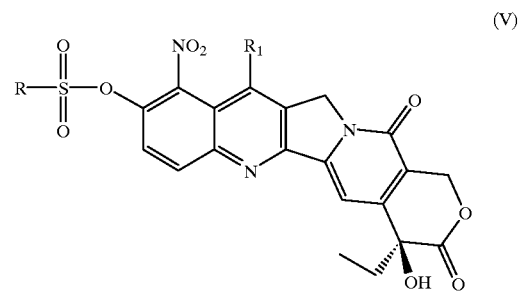

(V)

wherein R is 1-naphthyl, phenyl or p-methylphenyl and $R_1$ is as defined above;

(3) reducing the compound of formula (V) to form a compound of formula (Ia), (Ib) or (Ic); and, if desired, (4) converting a compound of formula (Ia), (Ib) or (Ic) into a pharmaceutically acceptable salt thereof.

A starting compound of formula (II) has a 20(S)-configuration which is retained throughout the process. A compound of formula (II) is typically free of the corresponding 20(R)-isomer. However, the present invention may be applied to a racemic mixture of a compound of formula (II)

or to the corresponding 20(R)-isomer. In that case, a racemic mixture of derivatives of 20(S)-camptothecin or 20(R)-camptothecin of formula (Ia), (Ib) or (Ic) is obtained. 10-Hydroxy-20(S)camptothecin may be obtained by known methodologies from 20(S)-camptothecin; see, for instance, JP-A59-51288, JP-A-59-51299; J. Med. Chem. 34, 98, 1991; and Chem. Pharm. Bull. 1991, 39, 3183, 1991.

9-amino-10-(1-naphthylsulfonyloxy)-20(S)-camptothecin (compound (1a)) in pure form or substantially free of 9-amino-10-(1-naphthylsulfonyloxy)-20(R)-camptothecin, 9-amino-10-phenylsulfonyloxy-20(S)-camptothecin (compound (1b)) in pure form or substantially free of 9-amino-10-phenylsulfonyloxy-20(R)-camptothecin and 7-ethyl-9-amino-10-(p-toluenesulfonyloxy)-20(S)-camptothecin (compound (1c)) in pure form or substantially free of 7-ethyl-9-amino-10-(p-toluenesulfonyloxy)-20(R)-camptothecin may be prepared by means of the above process, using as a starting material a compound of formula (II) in pure form or substantially free from the corresponding 20(R) isomer. Alternatively the above compounds of formula (1a), (1b) and (1c) which have a 20 (S) configuration may be isolated from a corresponding racemic mixture by known techniques.

The nitration described as step (1) may be carried out with a nitrating agent such as, e.g., nitric acid, a mixture of nitric and sulfuric acid, potassium nitrate or nitric acid and a boron trifluoride such as boron trifluoride monohydrate (see, for instance, Olah, G. A., et al. Synthesis 1085, 1992), nitric acid and trifluoromethansulfonic anhydride (ibid., 1087, 1992). Typically the reaction temperature is from about −20° C. to about 100° C. Typically, the reaction time may vary from a few minutes to several days such as from 5 minutes to 3 days, for example from 4 hours to 24 hours.

The conversion described as step (2) may be carried out, for example, by reacting a compound of formula (III) with a sulfonylating agent of formula (IV)

$$R—SO_2—R' \quad (IV)$$

wherein R is as defined above and R' is a leaving group, for example a halogen atom, an imidazolyl group, a —$OSO_2R$ or a —$N(C_6H_5)$ ($RSO_2$) group wherein R is as defined above. Preferably R' is a halogen atom such as fluoro, chloro or bromo, in particular chloro. Most preferably, the compounds of formula (IV) are: p-toluensulfonyl chloride, benzensulfonyl chloride or 1-naphthalenesulfonyl chloride. This reaction may be carried out, for example, at a temperature of from about −50° to about 100° C., for example from 0° to 50° C. Typically the reaction time may vary from 5 minutes to 3 days, for example from 4 hours to 24 hours. The reaction typically occurs in an anhydrous organic solvent such as, e.g., $CHCl_3$, $CH_2Cl_2$, tetrahydrofuran (THF), dioxane, dimethylformamide (DMF) or dimethylacetamide (DMA), optionally in the presence of an organic base such as, e.g. pyridine, triethylamine or a sterically hindered base such as, e.g. diisopropylethylamine or 2,6-dimethylpyridine may be present.

The conversion described in step (2) may also be carried out by reacting a compound of formula (III) with another suitable group known in the art which is capable of reacting with a phenyl to give a sulphonate.

The reduction described as step (3) may be carried out with a suitable reducing agent such as, e.g., molecular hydrogen, ammonium formate, triethylammonium formate, formic acid, tributyltin hydride, cyclohexadiene or a polymethylhydroxysilane, in the presence of a suitable catalyst such as, e.g., palladium, platinum oxide, platinum, rhodium or ruthenium as such, or supported on a suitable medium, such as, e.g., on carbon, $CaCO_3$, $BaSO_4$, or alumina. Suitable solvents for the reduction are organic solvents, such as, e.g., DMF, MeOH, acetic acid, $CHCl_3$, dioxane, THF or mixtures thereof. Typically the temperature is from about 0° C. to about 200° C. Typically, the reaction time is from about 5 minutes to about 12 hours.

Preferably, the nitration described as step (1) may be carried out with a nitrating agent such as nitric acid, mixtures of nitric and sulphuric acid, potassium nitrate or nitric acid and boron trifluoride monohydrate, or nitric acid and trifluoromethanesulfonic anhydride, at a temperature of from about −20° C. to about 60° C. Typically the reaction time is from a few minutes to several hours such as from 5 minutes to 12 hours.

Preferably, the conversion described as step (2) may be carried out in an anhydrous organic solvent such, e.g., $CHCl_3$, $CH_2Cl_2$, THF, dioxane, DMF or DMA; at a temperature of from −20° C. to 80° C., most preferably from −20° C. to 60° C.; for a period of from a few minutes, such as 5 minutes, to 2 days, most preferably from 5 minutes to 1 day; optionally in the presence of a base such as, e.g., pyridine, triethylamine or a sterically hindered base such as diisopropylethylamine or 2,6-dimethyl-pyridine, most preferably pyridine, triethylamine or diisopropylethylamine.

Preferably, the reduction described as step (3) may be carried out with a reducing agent such as molecular hydrogen, ammonium formate, triethylammonium formate, formic acid, tributyltin hydride, cyclohexadiene or a polymethylhydroxysilane, in the presence of a suitable catalyst such as, e.g., palladium, platinum oxide or platium as such, or supported on a suitable medium such as carbon, $CaCO_3$, $BaSO_4$ or alumina; at a temperature of from about 20° C. to about 120° C.; for a time which may vary from 1 hour to 12 hours.

The compounds of formulae (Ia), (Ib) and (Ic) are endowed with antitumor activity; for example, they are effective against leukaemia and solid tumors such as, for example colon and rectal tumors.

The antitumor activity of the compounds of the present invention is shown, for example, by the fact that they have been found to possess cytotoxic activity (expressed as the concentration producing 50% inhibition of cellular growth—$IC_{50}$), when tested in vitro on L1210 cells (murine lymphocytic leukemia) after 48 h continuous treatment with gradual concentrations of each molecule. The $IC_{50}$ was determined for each compound of formula (Ia), (Ib) and (Ic) from dose-response curves counting the total number of cells with a Coulter Counter (Kontron mod. ZM).

The tested compounds were dissolved in dimethylsulfoxide (DMSO) at a final concentration of 0.5%. The percentage of DMSO in solution does not affect the cellular growth. The obtained results are reported in the Table 1 below.

TABLE 1

| COMPOUND | * IC50 ng/mL |
|---|---|
| Formula (Ia) | 2.2 ± 0.3 |
| Formula (Ib) | 6.8 ± 0.4 |
| Formula (Ic) | 4.6 ± 0.1 |

* Concentration inhibiting 50% of cell growth.

A human or animal may thus be treated by a method which comprises the administration thereto of a pharmaceutically effective amount of a compound of formula (Ia), (Ib) or (Ic) or a salt thereof. The condition of the human or animal can thereby be improved.

The compounds of the invention can be administered in a variety of dosage forms, e.g. orally, in the form of tablets, capsules, lozengers, liquid solutions or suspensions; rectally, in the form of suppositories; parenterally, e.g. intramuscularly, intravenously, intradermally or subcutaneously.

The dosage depends on the age, weight and conditions of the patient and on the administration route.

For example, a suitable dosage for administration to adult humans may range from about 0.1 to 60 mg per Kg of body weight, a particulaly preferred range may be from about 1 to about 40 mg per Kg of body weight.

The present invention also includes a pharmaceutical composition which comprises a compound of formula (Ia), (Ib) or (Ic) as an active substance, in association with one or more pharmaceutically acceptable excipients.

The pharmaceutically compositions of the invention are usually prepared following conventional methods and are administered in a pharmaceutically suitable form.

For instance, solutions for intravenous injection or infusion may contain as carrier, tor example, sterile water or preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate or glycols, e.g. propylene glycol, and if desired, a suitable amount of lidocaine hydrochloride.

The solid oral forms, e.g. tablets and capsules, may contain, together with the active compound, diluents, e.g. lactose, dextrose, saccharose, cellulose, corn starch and or potato starch; lubricants, e.g. silica, talc, stearic acid, magnesium or calcium stearate and/or polyethylene glycols; binding agents, e.g. starches, arabic gums, gelatin, methylcellulose, carboxymethyl cellulose and polyvinylpyrrolidone; disaggregating agents, e.g. a starch, alginic acid, alginates, sodium starch glycolate; effervescing mixtures; diestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

The following Examples illustrate the preparation of the intermediates and compounds of the present invention and do not limit the scope of the invention.

EXAMPLE 1

9-nitro-10-hydroxy-20(S)-camptothecin (Method A)

50 ml of 35% $H_2O_2$ dropped into a suspension of 2.8 g of 20(S)-camptothecin in acetic acid. The temperature of the solution was raised to 80° C. and maintained for 3.5 hr. After cooling the solvent was evaporated until about 20 ml remain. The mixture was poured into 200 ml of water and ice. The precipitate was filtered, washed with water and ether and dried. The product was crystallized ($CHCl_3$/hexane) to give 1.9 g of 20(S)-camptothecin 1-oxide.

0.65 g of 20(S)-camptothecin 1-oxide was dissolved in 600 ml of dioxane, 8.8 ml of 1M $H_2SO_4$ were added and the solution was irradiated for 50 minutes (high pressure Hg lamp with a pyrex filter). The solvent was evaporated and the so obtained 10-hydroxy camptothecin was used for the following step (nitration) without any other purification.

The 10-hydroxy-20(S)-camptothecin was dissolved in 40 ml of $HNO_3$ (30%); after 1 hr 4 ml of $HNO_3$ (65%) were added.

The reaction mixture was left at room temperature for 18 hours and then was extracted with $CH_2Cl_2$. The organic phase was washed with water till neutral, dried with $Na_2SO_4$ and evaporated to give 0.250 g of the title product.

$N^1$NMR (DMSO-$d_6$), δ ppm: 0.86 (3H, t, J=7.3 Hz); 1.84 (2H, m); 5.23 (2H, s); 5.40 (2H, s); 6.51 (1H, s); 7.26 (1H, s); 7.6–8.2 (2H, m); 8.42 (1H, s).

Method B

A suspension of 20(S)-camptothecin (1 g) and prereduced $PtO_2$ (0.2 g) in a 1:1 mixture of acetic acid-dioxane (200 ml) was hydrogenated at room temperature and pressure until the mixture had adsorbed 2 equivalents of $H_2$. The suspension was filtered and the obtained solution was evaporated in vacuo to hield 0.6 g of a tetrahydroderivatives mixture.

Lead tetraacetate (2.1 g) was added to the crude tetrahyroderivative mixture (0.5 g) in trifluoroacetic acid (15 ml). The mixture was stirred at room temperature for 15 minutes, and then evaporated in vacuo. The crude 10-hydroxy-20(S)-camptothecin obtained was utilized for the subsequent step without further purification.

The 10-hydroxy-20(S)-camptothecin was dissolved in 40 ml of $HNO_3$ (30%); after 1 hr 4 ml of $HNO_3$ (65%) were added.

The reaction was washed with water till neutral, dried with $Na_2SO_4$ and evaporated to give 0.250 g of the title product, which was identifical to the compound obtained with method A.

According to analogous procedure, the following compound may be prepared:

7-ethyl-9-nitro-10-hydroxy-20(S)-camptothecin

1H-NMR (200 MH, DMSO-d6) δ (ppm): 0.86 (t, J=7.0 Hz, 3H), 1.18 (t, J=7.0 Hz, 3H), 1.84 (m, 2H), 2.84 (m, 2H), 5.31 (s, 2H), 5.41 (s, 2H), 6.51 (s, 1H), 7.26 (s, 1H), 7.64 (d, J=9.2, Hz, 1H), 8.23 (d, J=9.2 Hz, 1H), 11.90 (bs, 1H)

EXAMPLE 2

1 g of 9-nitro-10-hydroxy-20(S)-camptothecin is dissolved in 50 ml of $CH_2Cl_2$; 0.374 ml of $Et_3N$ and 0.665 mg of 1-naphthalensulfonyl chloride are added sequentially. After 1 h (HPLC monitoring) the reaction is worked up washing with HCl 5% then with water till neutrality; the organic phase is dried with $Na_2SO_4$, the solvent is evaporated and the product purified by flash chromatography to give 0.860 g of 9-nitro-10-(1-naphthylsulfonyloxy)-20(S)-camptothecin.

1H-NMR (400 MH, DMSO-d6) d (ppm): 0.84 (t, J=7.3 Hz, 3H), 1.83 (m, 2H), 5.23 (s, 2H), 5.41 (m, 2H), 6.55 (s, 1H), 7.34 (s, 1H), 7.61 (d, J=9.4 Hz, 1H), 7.7–8.6 (m, 7H), 8.42 (dd, J=0.9, 9.4 Hz, 1H), 8.52 (d, J=0.9 Hz, 1H). FD-MS (EHC=30 mA): m/z 599 (19%, M+); 409 (100%); 191 (51%).

EXAMPLE 3

To a degassed solution of 0.580 g of 9-nitro-10-(1-naphthylsulfonyloxy)-20(S)-camptothecin in 20 ml of DMF, 0.160 g of Pd/C 5% are added. The mixture is hydrogenated for 3 hr at room temperature then it is filtered on celite washing sequentially with DMF, $CH_2Cl_2$ and $CH_3OH$. The solvents are evaporated and the product purified by flash chromatography to give 0.280 g of 9-amino-10-(1-naphthylsulfonyloxy)-20(S)-camptothecin.

1H-NMR (400 MH, DMSO-d6) d (ppm): 0.84 (t, J=7.3 Hz, 3H), 1.83 (m, 2H), 5.22 (s, 2H), 5.39 (s, 2H), 5.95 (bs, 2H), 6.49 (s, 1H), 6.98 (d, J=9.4 Hz, 1H), 7.15 (d, J=9.4 Hz, 1H), 7.25 (s, 1H), 7.6–8.8 (m, 7H), 8.85 (s, 1H). FD-MS (EHC=30 mA): m/z 569 (66%, M+); 525 (14%); 379 (70%); 191 (100%).

EXAMPLE 4

1 g of 9-nitro-10-hydroxy-20(S)-camptothecin is dissolved in 50 ml of $CH_2Cl_2$; 0.374 ml of $Et_3N$ and 0.520 mg of benzenesulfonyl chloride are added sequentially. After 1 hr the reaction is worked up washing with HCl 5% then with water till neutrality; the organic phase is dried with Na$_2$SO$_4$, the solvent is evaporated and the product purified by flash chromatography to give 0.976 g of 9-nitro-10-(benzenesulfonyloxy)-20(S)-camptothecin.

1H-NMR (200 MH, DMSO-d6) d (ppm): 0.85 (t, J=7.3 Hz, 3H), 1.84 (m, 2H), 5.26 (s, 2H), 5.42 (s, 2H), 6.56 (s, 1H), 7.37 (s, 1H). 7.6–8.0 (m, 6H), 8.52 (dd, J=0.8, 9.3 Hz, 1H), 8.59 (d, J=0.8 Hz, 1H). FD-MS (EHC=29 mA): m/z 549 (100%, M$^+$); 408 (17%); 141 (13%).

EXAMPLE 5

To a degassed solution of 0.60 g of 9-nitro-10-(benzenesulfonyloxy)-20(S)-camptothecin in 15 ml of DMF, 0.090 g of Pd/C 10% are added. The mixture is hydrogenated for 3 hr at room temperature then it is filtered on celite washing sequentially with DMF, CH$_2$Cl$_2$ and CH$_3$OH. The solvents are evaporated and the product purified by flash chromatography to give 0.130 g of 9-amino-10-(benzenesulfonyloxy)-20(S)-camptothecin.

1H-NMR (200 MH, DMSO-d6) d (ppm): 0.85 (t, J=7.2 Hz, 3H), 1.84 (m, 2H), 5.23 (s, 2H), 5.40 (s, 2H), 5.99 (bs, 2H), 6.50 (s, 1H), 7.27 (s, 1H), 7.28 (d, J=9.2 Hz, 1H), 7.46 (d, J=9.2 Hz, 1H), 7.5–8.0 (m, 5H), 8.83 (s, 1H). FD-MS (EHC=28 mA): m/z 519 (100%, M$^+$); 379 (15%); 141 (8%).

EXAMPLE 6

1.5 g of 7-ethyl-9-nitro-10-hydroxy-20(S)-camptothecin is dissolved in 160 ml of CH$_2$Cl$_2$; 1.2 ml of Et$_3$N and 1 g of p-toluensulfonyl chloride are added sequentially. After 1.5 h the reaction is worked up washing with HCl 5% then with water till neutrality; the organic phase is dried with Na$_2$SO$_4$, the solvent is evaporated and the product purified by flash chromatography to give 1.6 g of 7-ethyl-9-nitro-10-(p-toluensulfonyloxy)-20(S)-camptothecin.

1H-NMR (200 MH, DMSO-d6) d (ppm): 0.85 (t, J=7.3 Hz, 3H), 1.11 (t, J=7.7 Hz, 3H), 1.86 (m, 2H), 2.43 (s, 3H), 2.79 (m, 2H), 5.34 (s, 2H), 5.43 (s, 2H), 6.56 (s, 1H), 7.34 (s, 1H), 7.5–7.9 (m, 4H), 7.97 (d, J=9.4 Hz, 1H), 8.49 (d, J=9.4 Hz, 1H). FD-MS (EHC=29 mA): m/z 591 (41%, M$^+$); 436 (19%); 155(100%).

EXAMPLE 7

To a degassed solution of 0.500 g of 7-ethyl-9-nitro-10-(p-toluensulfonyloxy)-20(S)-camptothecin in 10 ml of DMF, 0.10 g of Pd/C 10% are added. The mixture is hydrogenated for 4 hr at room temperature then it is filtered on celite washing sequentially with DMF, CH$_2$Cl$_2$ and CH$_3$OH. The solvents are evaporated and the product purified by flash chromatography to give 0.240 g of 7-ethyl-9-amino-10-(p-toluensulfonyloxy)-20(S)-camptothecin.

1H-NMR (200 MH, DMSO-d6) d (ppm): 0.85 (t, J=7.4 Hz, 3H), 1.02 (t, J=7.4 Hz, 3H), 1.86 (m, 2H), 2.35 (s, 3H), 3.18 (m, 2H), 5.23 (bs, 2H), 5.24 (s, 2H), 5.40 (s, 2H), 6.49 (s, 1H), 7.23 (s, 1H), 7.3–7.5 (m, 5H), 7.38 (d, J=8.5 Hz, 1H), 7.79 (d, J=8.5 Hz, 1H). FD-MS (EHC=30 mA): m/z 561 (100%, M$^+$); 407 (49%); 155 (11%).

We claim:

1. A compound of formula (Ia), (Ib) or (Ic):

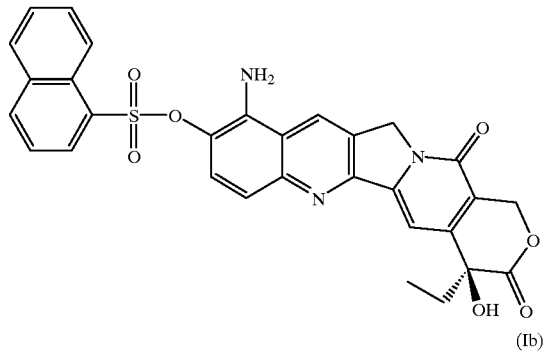

(Ia)

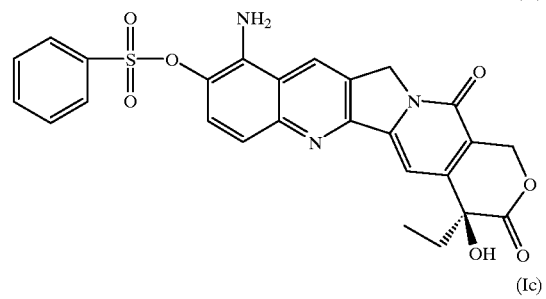

(Ib)

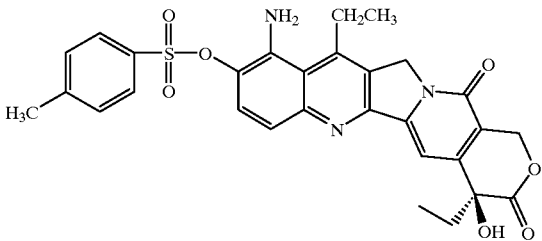

(Ic)

and the pharmaceutically acceptable salts thereof.

2. A process for preparing a compound as claimed in claim 1 which comprises:

(1) nitrating with a nitrating agent selected from the group consisting of nitric acid, mixtures of nitric and sulfuric acid, potassium nitrate, mixtures of nitric acid and a boron trifluoride, and mixtures of nitric acid and trifluoromethane sulfonic anhydride, a compound of formula (II)

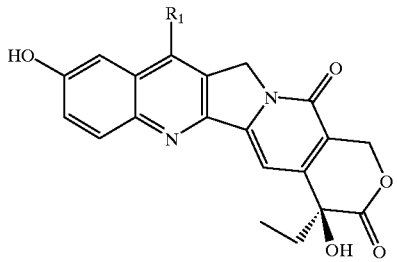

(II)

wherein R$_1$ is hydrogen or ethyl, to obtain a compound of formula (III)

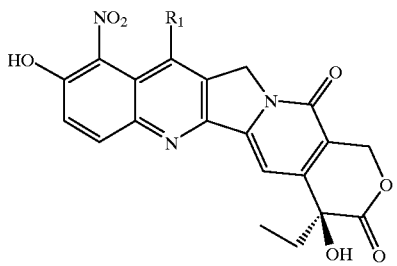

(III)

wherein $R_1$ is as defined above;

(2) isolating the compound of formula (III) and reacting said compound of formula (III) with a sulfonylating agent to form a compound of formula (V):

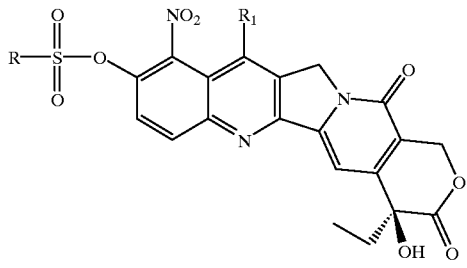

(V)

wherein R is 1-naphthyl, phenyl or p-methylphenyl and $R_1$ is as defined above;

(3) isolating and reducing the compound of formula (V) to form a compound of formula (Ia), (Ib) or (Ic); and, if desired, (4) converting a compound of formula (Ia), (Ib), or (Ic) into a pharmaceutically acceptable salt thereof.

3. A process as claimed in claim 2 wherein step (2) is conducted by reacting the compound of formula (III) with a sulfonylating agent of formula (IV):

R—SO$_2$—R'   (IV)

wherein R is 1-naphthyl, phenyl or p-methylphenyl and R' is a leaving group.

4. A process according to claim 3 wherein the leaving group R' is a halogen atom, an imidazolyl group, a —OSO$_2$R group or a —N(C$_6$H$_5$)(RSO$_2$) group wherein R is 1-naphthyl, phenyl or p-methylphenyl.

5. A pharmaceutical composition which comprises an antileukemia or antitumor susceptable to camtothecin effective amount of a compound as claimed in claim 1, in association with a pharmaceutically acceptable excipient.

6. A method of inhibiting the growth of leukemia or cells of tumors susceptable to camptothecin and/or killing leukemia or said cells of tumors, comprising contacting the leukemia or said cells of tumors with an effective amount of the compound of claim 1.

7. A method of treating a patient afflicted with leukemia or a tumor susceptable to camptothecin, comprising administering to the patient an amount of the compound of claim 1 effective for inhibiting the growth of the leukemia or tumor and/or killing the leukemia or tumor cells.

8. The compound or its pharmaceutically acceptable salt of claim 1, and having the formula (Ia).

9. The compound or its pharmaceutically acceptable salt of claim 1, and having the formula (Ib).

10. The compound or its pharmaceutically acceptable salt of claim 1, and having the formula (Ic).

* * * * *